(12) United States Patent
Mouw

(10) Patent No.: US 8,118,821 B2
(45) Date of Patent: Feb. 21, 2012

(54) MAGNETIC ANASTOMOSIS DEVICE HAVING IMPROVED DELIVERY

(75) Inventor: Steven Mouw, Santa Clara, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 572 days.

(21) Appl. No.: 12/247,802

(22) Filed: Oct. 8, 2008

(65) Prior Publication Data

US 2009/0125042 A1   May 14, 2009

Related U.S. Application Data

(60) Provisional application No. 60/978,754, filed on Oct. 9, 2007.

(51) Int. Cl.
 *A61B 17/08* (2006.01)
(52) U.S. Cl. ....................................................... 606/153
(58) Field of Classification Search .................. 606/151, 606/153, 155, 156, 213, 215; 182/899; 600/12, 600/37
See application file for complete search history.

(56) References Cited

U.S. PATENT DOCUMENTS

| 4,665,906 | A | | 5/1987 | Jervis |
| 5,454,834 | A | * | 10/1995 | Boebel et al. ................ 606/228 |
| 5,690,565 | A | | 11/1997 | Cope et al. |
| 5,690,656 | A | | 11/1997 | Cope et al. |
| 6,352,543 | B1 | | 3/2002 | Cole |
| 6,652,540 | B1 | | 11/2003 | Cole et al. |
| 6,719,768 | B1 | | 4/2004 | Cole et al. |
| 6,932,827 | B2 | | 8/2005 | Cole |
| 7,431,726 | B2 | * | 10/2008 | Spence et al. ................ 606/151 |
| 2005/0283235 | A1 | * | 12/2005 | Kugler et al. .............. 623/14.13 |
| 2008/0051626 | A1 | * | 2/2008 | Sato et al. .................... 600/101 |
| 2010/0099947 | A1 | | 4/2010 | Sato et al. |

FOREIGN PATENT DOCUMENTS

| EP | 1493391 A1 | 1/2005 |
| EP | 1 894 514 A2 | 3/2008 |
| FR | 2 760 627 A1 | 9/1998 |
| WO | WO 81/00668 | 3/1981 |
| WO | WO 2005/065412 A2 | 7/2005 |

OTHER PUBLICATIONS

International Search Report; PCT/US2008/079206 (Nov. 24, 2008).

* cited by examiner

*Primary Examiner* — Corrine M McDermott
*Assistant Examiner* — Dianne Dornbusch
(74) *Attorney, Agent, or Firm* — Brinks Hofer Gilson & Lione

(57) ABSTRACT

A magnet assembly for a magnetic anastamosis device is provide that is minimally invasive, easily and quickly delivered, and is accurately positioned to improve the delivery procedure. The magnet assembly includes an elongated hub and a plurality of magnetic members disposed over the elongated hub. The elongated hub is formed of a resilient or shape memory material, permitting the magnet assembly to be operable between a delivery configuration and a deployed configuration. In this manner, the package width of the magnet assembly is greatly reduced for delivery, thereby permitting delivery over a wire guide as well as through an access device such as a catheter. Associated delivery procedures and medical devices are also provided.

19 Claims, 6 Drawing Sheets

MAGNETIC ANASTOMOSIS DEVICE HAVING IMPROVED DELIVERY

CROSS-REFERENCE TO RELATED APPLICATIONS

This application claims the benefit of U.S. Provisional Application Ser. No. 60/978,754, filed on Oct. 9, 2007, entitled "MAGNETIC ANASTOMOSIS DEVICE HAVING IMPROVED DELIVERY"

FIELD OF THE INVENTION

The present invention relates generally to magnetic anastomosis devices for forming an anastomosis between two viscera.

BACKGROUND OF THE INVENTION

Magnetic anastomosis devices (MADs) are currently used to create a channel between two viscera for the purpose of redirecting bodily fluids. For example, intestinal contents or bile may be redirected in patients who have developed an obstruction of the bowel or bile duct due to such conditions as tumor, ulcer, inflammatory strictures or trauma. With reference to FIG. 1, the relative positions of several organs of the abdominal cavity are shown, including the gall bladder 10, the common bile duct 12, the stomach 14, the duodenum 16 and the jejunum 18 of the small intestine. Inflammatory strictures 20, 22 of the jejunum 18 and bowel duct 12 are shown by the dotted lines in FIG. 1.

A magnetic anastomosis device (MAD) 30 has been depicted in FIG. 2, the details of which may be found in U.S. Pat. No. 5,690,656, the disclosure of which is incorporated herein by reference in its entirety. Generally, the MAD 30 includes first and second magnet assemblies 30a, 30b comprising magnetic cores 36a, 36b which are surrounded by thin metal rims 38a, 38b. Due to the magnetic attraction between the two magnetic cores 36a, 36b, the walls 32, 34 of two adjacent viscera may be sandwiched and compressed between the magnet assemblies 30a, 30b, resulting in ischemic necrosis of the walls 32, 34 to produce an anastomosis between the two viscera. With reference back to FIG. 1, the two viscera may comprise the jejunum 18 and the stomach 14, the bowel duct 12 and the duodenum 16, or various other combinations.

Historically, MADs have been delivered through surgical intervention such as laparotomy, which of course is invasive and carries its own risks. The exemplary self-centering MAD of U.S. Pat. No. 5,690,656 permit delivery of the device over a wire guide and through the oral cavity, and typically under fluoroscopy. Alternatively, delivery can be accomplished by simply swallowing the magnet assemblies of the MAD and using massage under fluoroscopy to center the two magnet assemblies. Finally, delivery of the magnet assemblies has occasionally been performed endoscopically with grasping forceps, which can be time consuming and difficult. Removal of the MAD is typically accomplished allowing the magnet assemblies to pass through the gastrointestinal track naturally, or more typically with a follow-up endoscopic procedure using grasping forceps. Unfortunately, the relatively large size of the magnet assemblies can make delivery and retrieval complicated. In fact, balloon dilation of bodily lumens is often required in order to deliver the magnet assemblies to the desired location. Likewise, the size of bodily lumens is often the limiting factor in the size of the magnet assemblies that can be delivered and deployed.

BRIEF SUMMARY OF THE INVENTION

The present invention provides a magnet assembly for a magnetic anastamosis device that is minimally invasive, easily and quickly delivered, and is accurately positioned to improve the delivery procedure. According to one embodiment constructed in accordance with the teachings of the present invention, a magnet assembly for a magnetic anastamosis device includes an elongated hub and a plurality of magnetic members disposed over the elongated hub. The elongated hub is formed of a shape memory material, permitting the magnet assembly to be operable between a delivery configuration and a deployed configuration. In the delivery configuration, the elongated hub extends generally linearly, and in the deployed configuration the elongated hub forms an annular shape. In this manner, the package width of the magnet assembly is greatly reduced for delivery, thereby permitting delivery over a wire guide as well as through an access device such as a catheter.

According to more detailed aspects, the elongated hub is formed of a nickel titanium alloy. The elongated hub is preferably tubular and defines an inner passageway sized to receive the wire guide. The plurality of magnetic members may abut each other in the deployed configuration. Each of the plurality of magnetic members includes a hole sized to receive the elongated hub, and each hole may be sized to permit the magnetic member to slide along the elongated hub, or may be sized to provide a friction fit. In the former case, the elongated hub includes a stop formed at one end of the elongated hub to prevent the plurality of magnetic members from passing beyond the end. Alternatively, the plurality of magnetic members and elongated hub may include corresponding tabs and detents or other means for maintaining the position of the magnetic members on the elongated hub. In one form, the plurality of magnetic members each include a jacket attached to a side thereof, each jacket projecting beyond the sides to define an edge. Each edge may contact the edges of adjacent jackets to form a continuous annular "cutting" edge in the deployed configuration.

Another embodiment constructed in accordance with the teachings of the present invention provides a medical device for forming an anastamosis between two bodily walls, the medical device comprising a magnet assembly and an access device. The magnet assembly has an elongated hub and a plurality of magnetic members disposed over the elongated hub. The access device is structured to be coupled to the magnet assembly. The magnet assembly is biased to a deployed configuration defined by the elongated hub and plurality of magnetic members forming an annular shape. When the magnet assembly is coupled to the access device, the magnet assembly assumes a delivery configuration defined by the elongated hub and plurality of members having a generally linear configuration. According to more detailed aspects, the elongated hub is formed of a resilient material biased to the deployed configuration. Alternatively, the elongated hub is formed of a shaped memory material which takes the deployed configuration when the elongated hub is exposed to body temperature.

A method of delivering a magnet assembly that is part of a magnetic anastamosis device is also provided in accordance with the teachings of the present invention. A magnet assembly is provided having an elongated hub and a plurality of magnetic members disposed over the elongated hub. An access device is introduced to a position proximate a first bodily wall. The magnet assembly is coupled to the access device such that the magnet assembly assumes a delivery configuration having a generally linear shape. The magnet assembly is translated relative to the access device whereby the magnet assembly assumes a deployed configuration having a generally annular shape.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
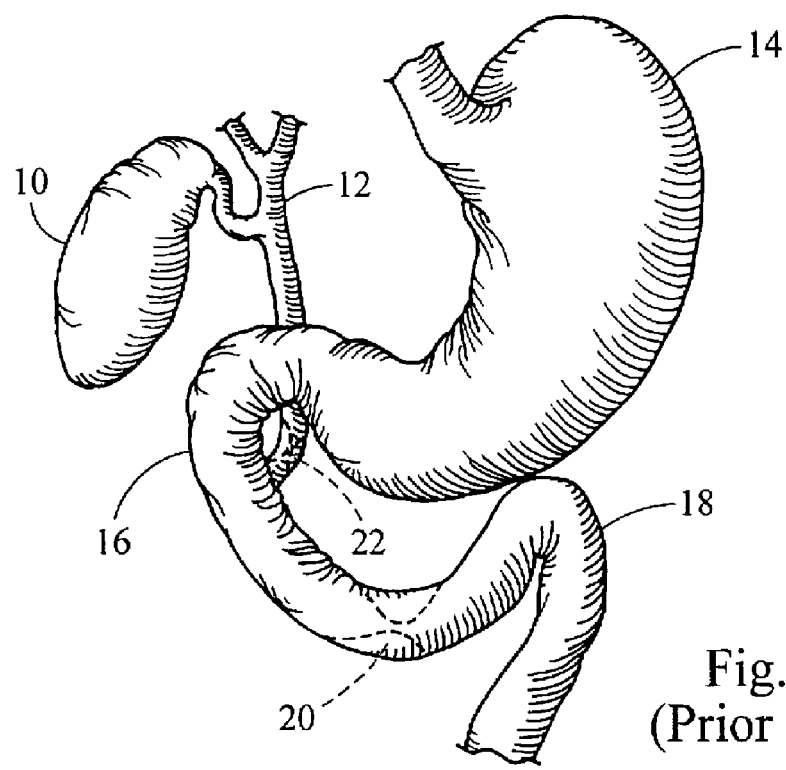
FIG. 1 depicts various abdominal organs.
Figure 2:
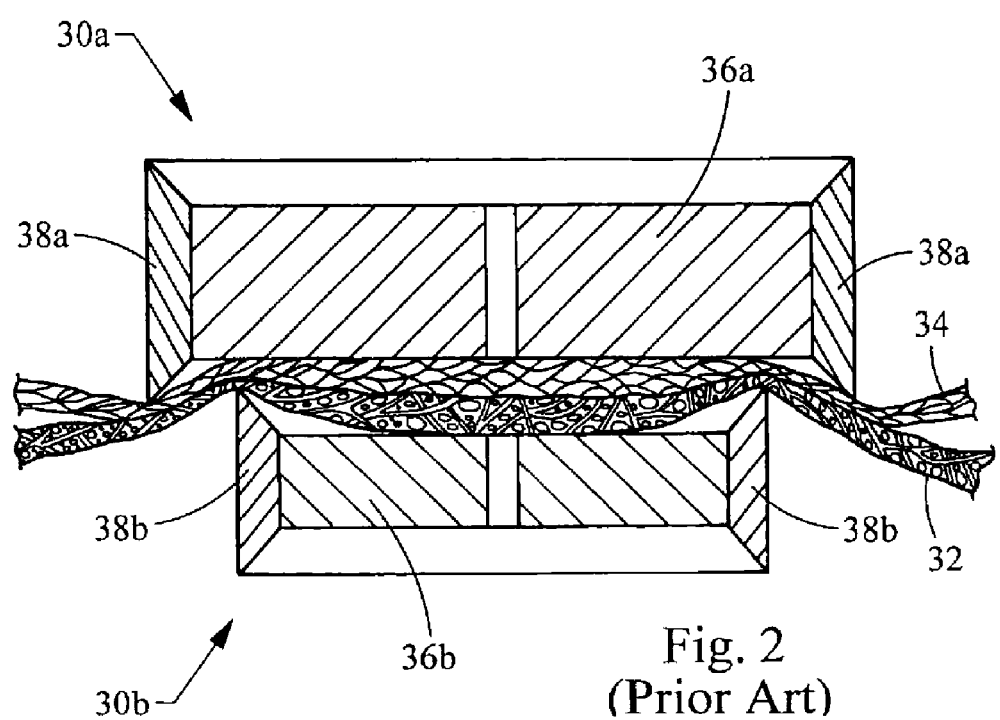
FIG. 2 depicts a prior art magnetic anastamosis device.
Figure 3:
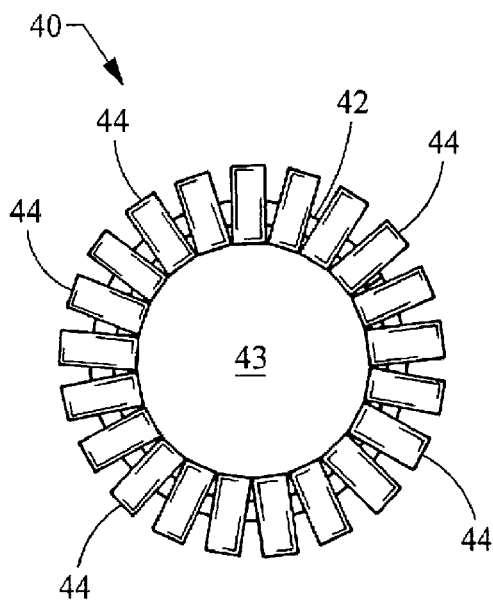
FIG. 3 depicts is a plan view of magnet assembly in a deployed configuration for forming a portion of a magnetic anastamosis device constructed in accordance with the teachings of the present invention.
Figure 6:
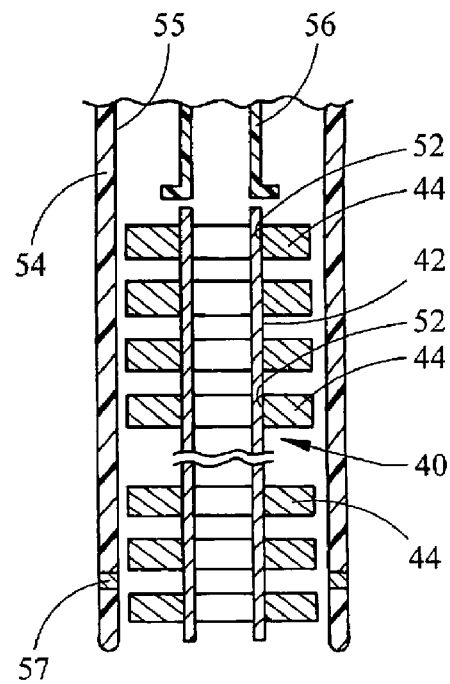
FIG. 6 is cross-sectional view of the delivery configuration of the magnet assembly depicted in FIG. 3.

Turning now to the figures, FIG. 3 depicts a single magnet assembly 40 for a magnetic anastomosis device that is used to form an anastomosis between two viscera. The magnet assembly 40 generally comprises an elongated hub 42 and a plurality of magnetic members 44 disposed over the elongated hub 42. The deployed configuration of the magnet assembly 40 is depicted in FIG. 3, wherein the elongated hub 42 and the plurality of magnetic members 44 form an annular shape having an interior space 43. It will be recognized by those skilled in the art that the magnet assembly 40 may be used in conjunction with another magnet assembly of larger or smaller size to form the magnetic anastamosis device (i.e. similar to that depicted in FIG. 2.) To improve delivery of the magnet assembly 40, the magnet assembly is operable to a delivery configuration as depicted in FIG. 6. In the delivery configuration, the magnet assembly 40 has a reduced width, making it easier to pass through bodily lumens.

Figure 4:
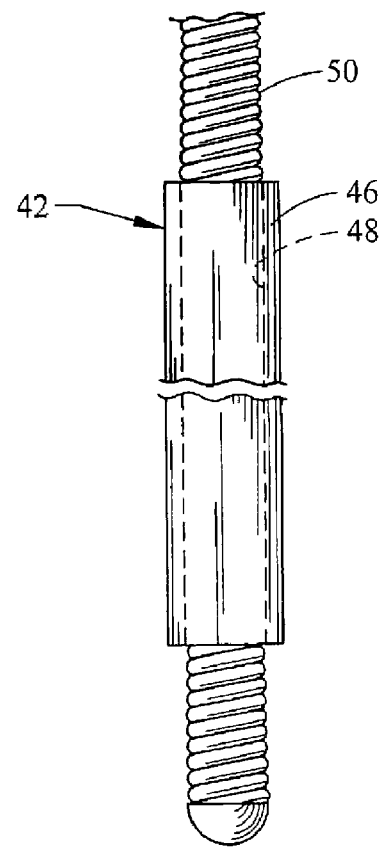
FIG. 4 is a plan view of the delivery condition of an elongated hub forming a portion of the magnet assembly depicted in FIG. 3.
Figure 5:
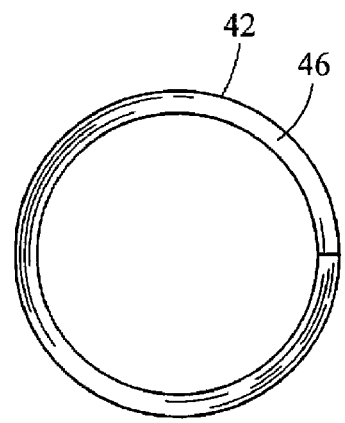
FIG. 5 is a plan view of the deployed condition of the elongated hub depicted in FIG. 4.

To achieve the delivery and deployed configurations of the magnet assembly 40, the elongated hub 42 is structured to transition between a linear condition as depicted in FIG. 4 and an annular condition such as the circular shape depicted in FIG. 5. As such, the elongated hub 42 may be constructed of a resilient material which is biased to the annular condition depicted in FIG. 5 but may be flexed and straightened into the linear condition depicted in FIG. 4. Suitable resilient materials include metals (e.g. stainless steel), alloys (e.g. nickel-titanium) or polymers (e.g. polyethylene, polytetrafluoroethylene (PTFE) including Teflon®, polyvinyl chloride (PVC)), and composites. Alternatively, the elongated hub 42 may be formed of a shape memory material such as nickel-titanium alloys (Nitinol), copper-aluminum-nickel, copper-zinc-aluminum, and iron-manganese-silicon alloys. That is, the shape memory material of the elongated hub 42 is structured to take the linear condition of FIG. 4 at a first temperature, and moves into the annular condition of FIG. 5 at a second temperature. The second temperature preferably corresponds to body temperature of the patient, or above body temperature but below tissue harming temperature, so that one can freely maneuver the device inside the body, and then inject a hot fluid over the device to trigger the shape memory. It will be recognized that the linear condition of the elongated hub 42 corresponds with the delivery configuration of the magnet assembly 40 (FIG. 6) while the annular condition of the elongated hub 42 corresponds to the deployed configuration of the magnet assembly 40 (FIG. 3).

As best seen in FIG. 4, the elongated hub 42 is preferably formed as a tube 46 defining an interior passageway 48 which is sized to receive an access device such as a wire guide 50. For example, the wire guide 50 may be used to maintain the linear condition of the elongated hub 42 when it is constructed of a resilient material that is biased to the annular condition (FIG. 5). In either construction of the elongated hub 42 (i.e. biased or shape memory), the ability to couple the elongated hub 46 and magnet assembly 40 to a wire guide 50 is useful in navigating the magnet assembly 40 to the desired location for forming the anastomosis. For example, it will be recognized by those skilled in the art that the wire guide 50 may include radiopaque markers permitting tracking of the distal tip of the wire guide 50 such that the delivery point of the magnet assembly 40 may be readily and easily monitored by the physician under fluoroscopy.

Turning to FIG. 6, it will be recognized that an alternate access device such as a catheter or cannula 54 may be used to maintain the magnet assembly 40 in its delivery configuration, while also providing access to the desired location within the viscera on which the procedure will be formed. The cannula 54 defines an interior space 55 receiving the magnet assembly 40 therein. A pusher 56 may be used to translate the magnet assembly 40 within the cannula 54 or simply to maintain its position therein. As with the wire guide 50, the cannula 54 may include radiopaque markers 57 permitting tracking of the access device under feroscopy for accurate positioning of the magnet assembly 40. It will also be recognized by those skilled in the art that the cannula 54 may be used alone or in conjunction with a wire guide 50 for navigation of the bodily lumens and delivery of the magnet assembly 40.

Figure 7:
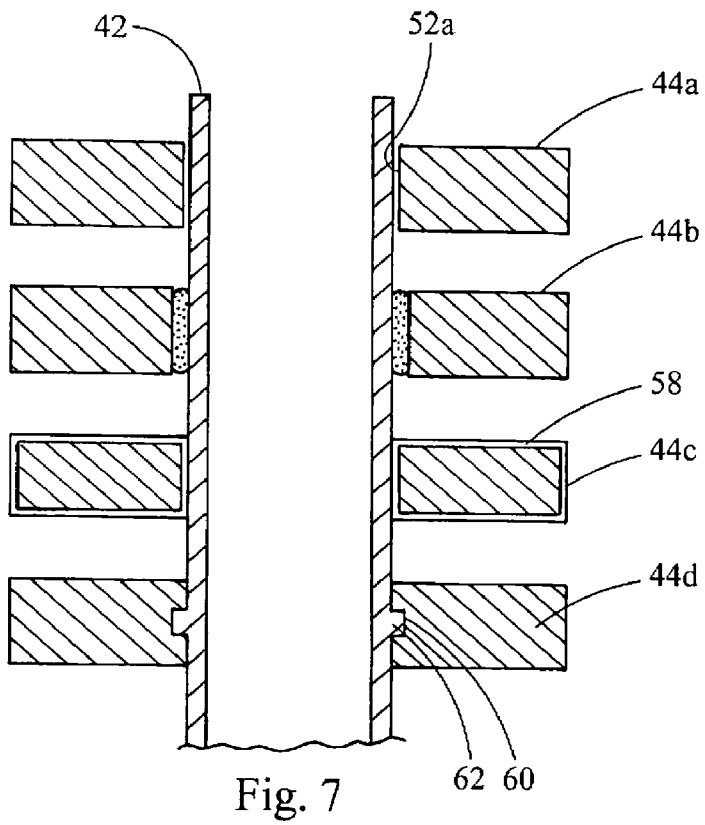
FIG. 7 is a cross-sectional view showing different means for connecting the magnetic members and the elongated hub to form the magnet assembly depicted in FIG. 3.
Figure 8:
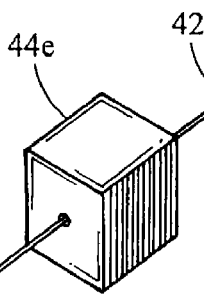
FIGS. 8 through 12 are perspective views showing various embodiments of magnetic members forming a portion of the magnet assembly in accordance with the teachings of the present invention.
Figure 9:
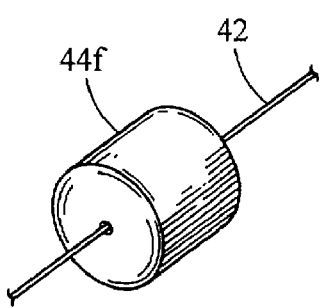
Figure 10:
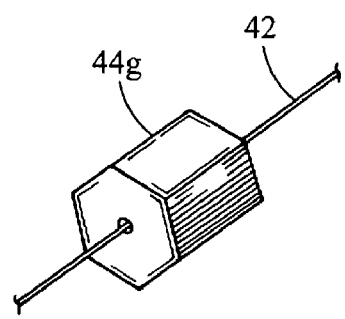

As also seen in FIG. 6, the plurality of magnetic members 44 are axially spaced along the elongated hub 42. In particular, each magnetic member 44 is located on the exterior of the elongated hub 42 and includes a hole 52 sized to receive the elongated hub 42. Turning to FIG. 7, a few of the numerous ways in which the magnetic members 44 may be coupled to the elongated hub 42 have been depicted. By way of example, magnetic member 44a includes a hole 52a which is sized larger than an outer diameter of the elongated hub 42 and thus is axially translatable therealong. The magnetic member 44b has been shown as soldered to the elongated hub 42, although numerous related means such as welding or adhesives may also be employed. The magnetic member 44c includes a protective coating 58 which may be formed of various materials such as polymers like Teflon® or Paralene® for protection of the magnetic core from the corrosive effects of digestive acids or other bodily fluids depending upon the body structure involved. It will also be recognized that the magnetic member 44c depicts a friction fit with the elongated hub 42, which may be employed regardless of whether the coating 58 is used. Finally, magnetic member 44d depicts a corresponding detent 60 and tab 62 which may be formed on the hub 42 and magnetic member 44d.

Figure 11:
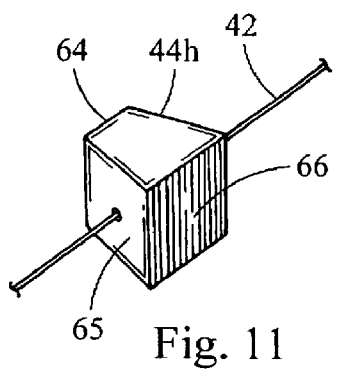
Figure 12:
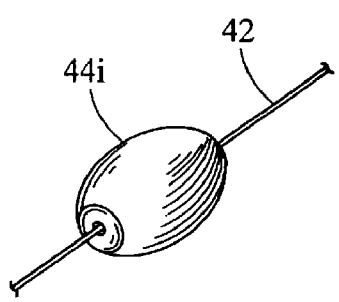

The magnet assembly 40 as depicted in FIGS. 3-7 has a general ring or disc shape (i.e. having an axial height which is less than the outer diameter of the magnetic member 44) which may be circular, oval or ovoid, square or the like, and it will also be recognized by those skilled in the art that the magnetic members 44 may take numerous sizes and shapes, a few of which have been depicted in FIGS. 8-12. The magnetic member 44e of FIG. 8 has been depicted as generally cubular. The magnetic member 44f of FIG. 9 has been depicted as generally cylindrical. The magnetic member 44g of FIG. 10 has been depicted as polygonal and specifically hexagonal, while also being elongated. The magnetic member 44h of FIG. 11 has been depicted as a generally trapezoidal body, the trapezoidal shape existing in a plane generally parallel to the elongated hub 42. The trapezoidal shape is denoted by a radially inner side 64 which is smaller in length than a larger radially outer side 66. It will be recognized by those skilled in the art that the trapezoidal shape of magnetic member 44h, as well as related wedge or pie shapes, has particular usefulness when a continuous upper or lower surface of the magnet assembly 40 is desired. That is, the angled side surfaces 65 will abut adjacent side surfaces 65 of the neighboring magnetic members 44h. As such, the angling of side surface 65 and the relative sizes of opposing surfaces 64, 66 may be selected depending upon the number of magnetic members 44h and the radius of the annular deployed configuration (FIG. 3). Finally, the magnetic member 44i of FIG. 12 is formed as an oblong bead. Numerous other shapes of the magnetic members 44 may be readily envisioned by those skilled in the art.

Figure 13:
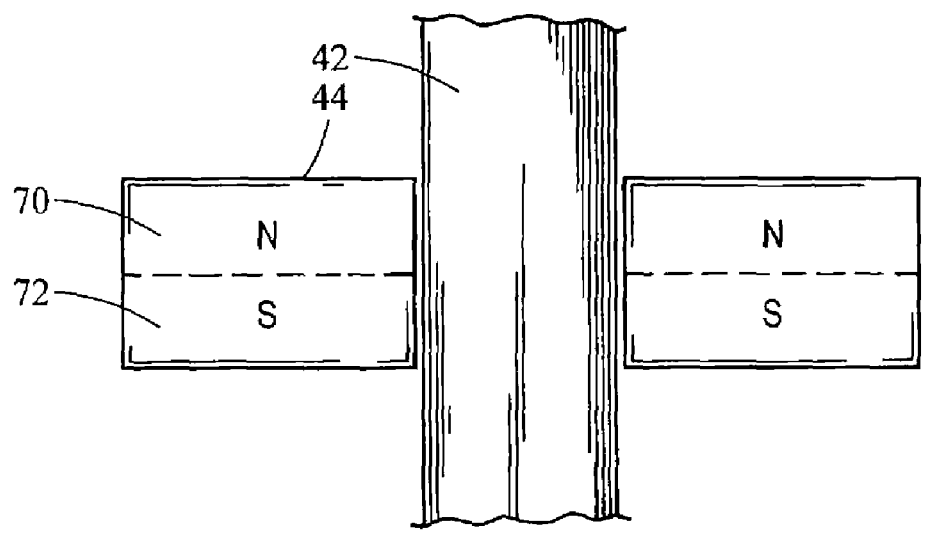
FIG. 13 is a schematic illustration of the magnetic orientation of the magnetic members.
Figure 14:
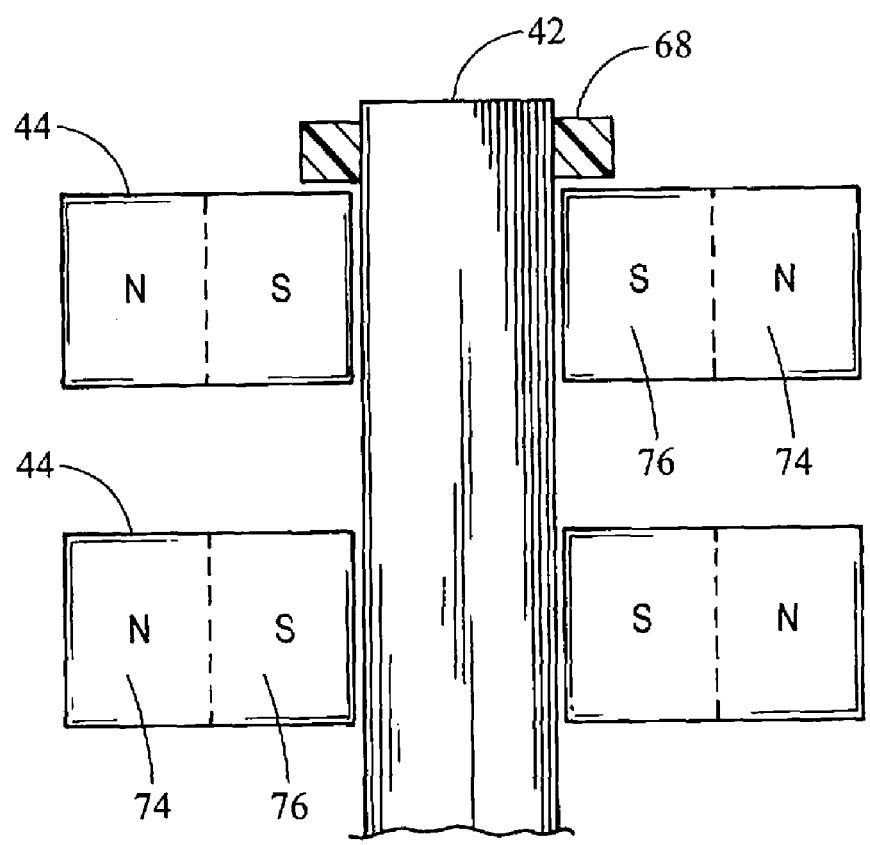
FIG. 14 is a schematic illustration, partially in cross-section, depicting another magnetic orientation of the magnetic members.
Figure 15:
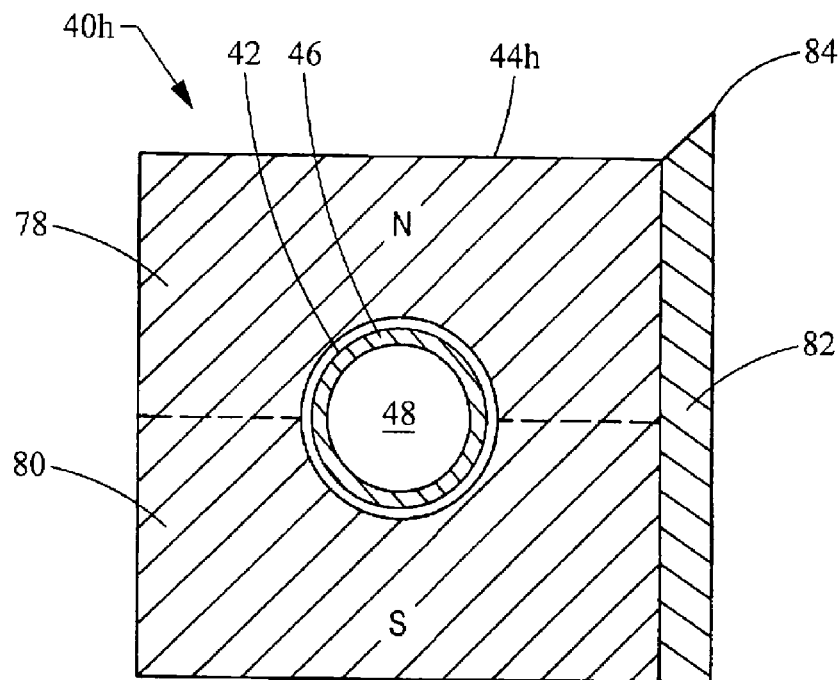
FIG. 15 is a plan view of another embodiment of a magnet assembly for forming a magnetic anastamosis device constructed in accordance with the teachings of the present invention.
Figure 16:
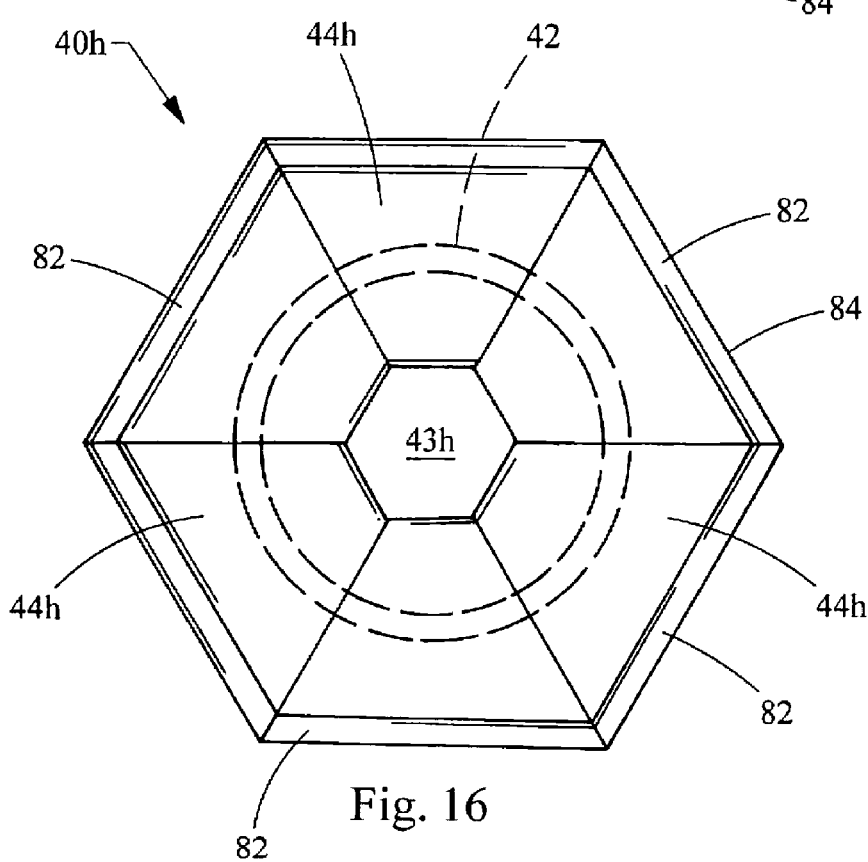
FIG. 16 is a cross-sectional view of the magnet assembly depicted in FIG. 15.

As shown in FIGS. 13, 14 and 15, each magnetic member 44 may be designed to have its magnetic north and south poles divided by virtually any plane. For example, in FIG. 13 the north portion 70 and south portion 72 of the magnetic member 44 has been separated along a transverse plane (indicated by dotted line), generally perpendicular to the axis of the elongated hub 42. In FIG. 14, each magnetic member 44 has its north portion 74 and south portion 76 divided along an annular plane (indicated by dotted line), generally parallel to the axis of the elongated hub 42. It will also be recognized that in the embodiment of FIG. 14, when the magnetic members 44 are permitted to slide axially over the elongated hub 42, a stop 68 may be formed at the ends of the elongated hub 42 to keep the magnetic members 44 disposed over the elongated hub 42. In FIG. 16, the magnetic member 44h has its north portion 78 separated from its south portion 80 by a longitudinal plane (indicated by dotted line) parallel with the axis of the elongated hub 42.

It can also be seen in FIGS. 15 and 16 that another embodiment of the magnet assembly 40h has been depicted which utilizes the trapezoidal magnetic members 44h of FIG. 11. As previously noted, the magnetic members 44h may be sized whereby in the deployed configuration the side surfaces 65 abut to form a continuous upper and lower annular surface, as best seen in FIG. 16. Again, the magnetic members 44h leave an interior space 43h in the deployed configuration. To accommodate the magnetic members 44h in both the delivery and deployed configurations, each member 44h includes an elongated hole 52h for receiving the elongated hub 42. Preferably the holes 52h have a width equal to or greater than an outer diameter of the elongated hub 42 so that the free ends of the hub 42 may be received side-by-side in the deployed configuration as depicted in FIG. 15. It will be recognized that the magnet assembly 40h is not limited to side-by-side free ends of the elongated hub 42, and by way of example the free ends could be telescopically received, structured for coaxial mating, or the elongated hub 42 constructed differently to accommodate the configurations, such as being formed of a flat wire or strip, of a material which stretches, or numerous other constructions.

It will also be recognized that the magnetic member 44h has been modified to include a jacket 82 attached to a side thereof, and particularly the larger radially outward surface 66 depicted in FIG. 11. Each jacket 82 projects beyond the adjacent sides (i.e. upper and lower sides on the page) to define an edge 84. As such, in the deployed configuration of FIG. 16, each edge 84 contacts the edges of adjacent jackets 82 to form a continuous annular edge in the deployed configuration. The coupling of magnet assembly 40h to another magnet assembly of smaller or larger size and having a similar flange 82 results in automatic self-centering, as well as the continuous edge of the smaller magnet assembly acting as a cutting edge in order to accelerate the process of ischemic necrosis of the tissue captured between the two magnets, thereby forming the anastamosis more quickly.

Figure 17:
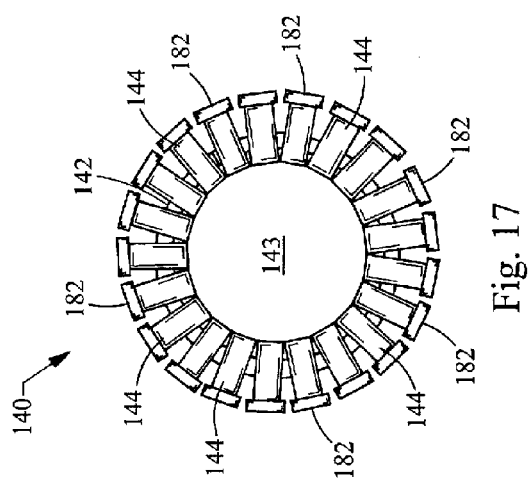
FIG. 17 depicts is a plan view of the magnet assembly of FIGS. 15 and 16 in a deployed configuration.

It will be recognized that the jackets 82 may be employed with any shape of magnetic members 44, and thus the edges 84 need not contact each other to form a continuous annular edge. For example, FIG. 17 depicts a magnet assembly 140 much like that of FIG. 3 wherein each of the magnetic members 144 includes a jacket 182 that is spaced from adjacent jackets 182, but nonetheless forms a sufficient cutting edge to accelerate ischemic necrosis. Alternatively, a longer magnet assembly 140 could be employed and the jackets 182 attached to the radially inner area of the magnetic members 144 so that a continuous annular edge is formed around the interior space 143.

Figure 18:
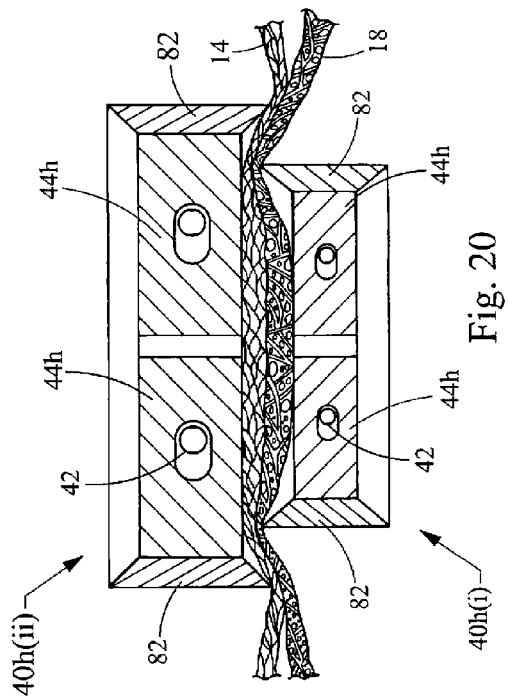
FIGS. 18-20 schematically depict delivery of two magnet assemblies for forming a magnetic anastamosis device in accordance with the teachings of the present invention.
Figure 20:
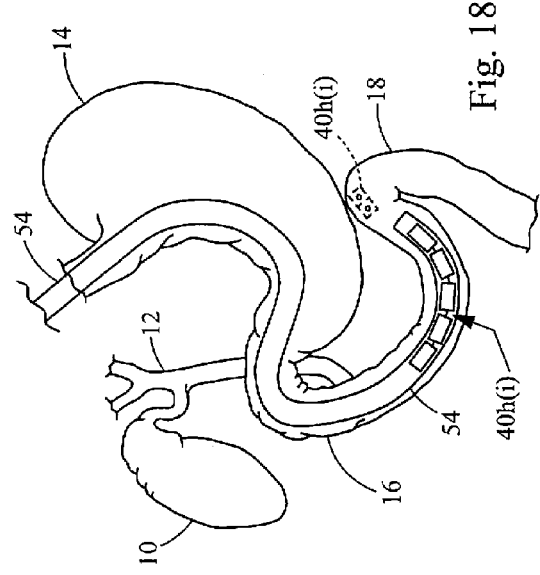
Figure 19:
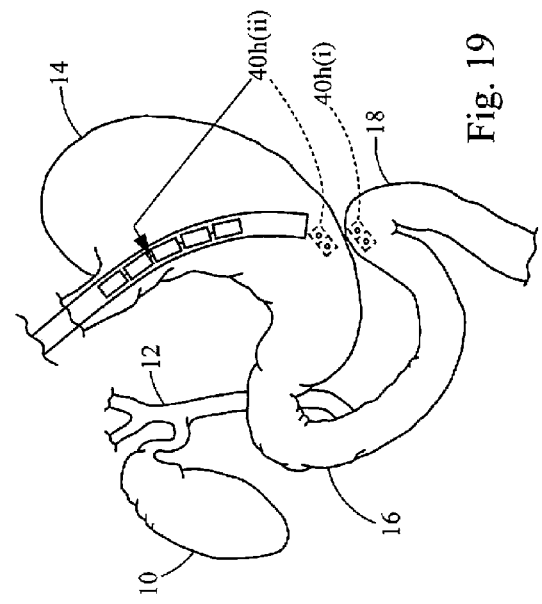

Although one magnet assembly 40, 140 has been described, two magnet assemblies are intended for use together as a magnetic anastamosis device, as previously indicated. At least one of the two magnet assemblies is a magnet assembly constructed in accordance with the teachings of the present invention. For example, FIG. 18 depicts a first magnet assembly 40h(i) (similar to the magnet assembly 40h depicted in FIGS. 15-16) being delivered into the duodenum 16 using the delivery catheter 54. In the figure, the deployed configuration of the magnet assembly 40h(i) has been illustrated in dashed lines. FIG. 19 depicts a second magnet assembly 40h(ii) being delivered into the stomach 14 using the delivery catheter 54, the second magnet assembly 40h(ii) having a different diameter than the first magnet assembly 40h(i), but otherwise being similarly constructed. As shown in the enlarged cross-sectional view of FIG. 20, the two magnet assemblies 40h(i), 40h(ii) become attracted together to sandwich the tissue 14, 16 therebetween, eventually causing necrosis of the tissue and an anastamosis. Further details of methods for delivering one or more magnet assembly are described hereinbelow.

Accordingly, it will be recognized by those skilled in the art that the magnetic anastamosis device employing the magnet assemblies 40 of the present invention not only preserves the benefits of improving the time to form an anastamosis, but further provides a smaller delivery configuration which may be easily located within the body for accurate delivery. As such, the present invention also encompasses a method for delivering the magnet assembly to a position for forming an anastamosis between two viscera. The method includes introducing an access device into one of the viscera, such as the wire guide 50 or cannula 54 depicted in FIGS. 4 and 6 respectively. The magnet assembly is coupled to the access device such that the magnet assembly takes the delivery configuration depicted in FIG. 6 where the elongated hub and plurality of magnetic members extend generally linearly. Upon translation of the magnet assembly relative to the access device, the magnet assembly takes a deployed configuration (FIG. 3, FIG. 15) within the viscera where the elongated hub and plurality of magnetic members form an annular shape. The access device may be placed within the viscera and then the magnet assembly be translated along the access device to the desired location, or the access device and magnet assembly may be coupled together and then translated together into the viscera. The combined medical device for performing an anastamosis between two viscera thus includes both the magnet assembly and the access device which cooperate together to permit the delivery of the magnet assembly to a desired location.

When the elongated hub 42 is simply biased to its annular condition (FIG. 5) the access device is used to maintain the elongated hub 42 in its linear condition and the magnet assembly 40 and its delivery configuration. Thus, upon decoupling of the magnet assembly and access device, the magnet assembly will automatically assume its deployed configuration. When the elongated hub 42 is formed of a shape memory material such as nitinol, the increased temperature of the patient's body will cause the elongated hub 42 to take its annular condition (FIG. 5) and the magnet assembly 40 will assume its deployed configuration (FIG. 3). Likewise, a lower temperature fluid may be delivered to the magnet assembly at a later time to cause it to resume its delivery configuration (FIG. 6) (or the material of the elongate hub 42 can be formed to include a stress induced martensite (SIM) phase such that sufficient stress on the hub 42 causes it to become more plastic and able to take the delivery configuration) whereby forceps or another device may be used to withdraw the magnet assembly onto a wire guide or within a cannula or other access device for removal from the patient. In both cases, upon formation of the anastamosis the magnets may be permitted to pass through the body naturally or may be removed by other means such as laporotic removal, endoscopic removal or other procedure.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A magnet assembly for a magnetic anastamosis device used for forming an anastamosis between two bodily walls, the magnet assembly comprising:
   an elongated hub having a proximal end and a distal end, the elongated hub being tubular and defining an inner passageway sized to receive a wire guide; and
   a plurality of magnetic members disposed over the elongated hub;
   the magnet assembly operable between a delivery configuration and a deployed configuration, the elongated hub extending generally linearly in the delivery configuration, the elongated hub forming an annular shape in the deployed configuration where the proximal end and the distal end of the elongated hub are adjacent to each other.

2. The magnet assembly of claim 1, wherein the plurality of magnetic members abut each other in the deployed configuration.

3. The magnet assembly of claim 1, wherein each of the plurality of magnetic members includes a hole sized to receive the elongated hub.

4. The magnet assembly of claim 3, wherein each hole is sized to permit the magnetic member to slide along the elongated hub.

5. The magnet assembly of claim 4, wherein the elongated hub includes a stop formed at one of the proximal end and the distal end of the elongated hub structured to prevent the plurality of magnetic members from passing beyond the end.

6. The magnet assembly of claim 1, wherein the plurality of magnetic members are fixed to the elongated hub.

7. The magnet assembly of claim 1, wherein the plurality of magnetic members and the elongated hub include corresponding tabs and detents to maintain the positions of the plurality of magnetic members along the elongated hub.

8. The magnet assembly of claim 1, wherein the plurality of magnetic members have a trapezoidal shape.

9. The magnet assembly of claim 1, wherein each of the plurality of magnetic members includes a jacket attached to a side thereof, each jacket projecting beyond the side to define an edge.

10. The magnet assembly of claim 9, wherein each edge contacts the edges of adjacent jackets to form a continuous annular edge in the deployed configuration.

11. The magnet assembly of claim 1, wherein the elongated hub is formed of a shape memory material.

12. A medical device for use in forming an anastamosis between two bodily walls, the medical device comprising:
   a magnet assembly having an elongated hub having a proximal end and a distal end and a plurality of magnetic members disposed over the elongated hub; and
   an access device structured to be coupled to the magnet assembly, the access device comprising a wire guide;
   wherein the elongated hub includes a passageway sized to receive the wire guide therein;
   the magnet assembly assuming a delivery configuration when the magnet assembly is coupled to the access device, the delivery configuration having a generally linear shape;
   the magnet assembly assuming a deployed configuration when the magnet assembly is decoupled from the access device, the deployed configuration having a generally annular shape where the proximal end and the distal end of the elongated hub are adjacent to each other.

13. The medical device of claim 12, wherein the elongated hub is formed of a resilient material biased to the deployed configuration.

14. The medical device of claim 12, wherein the elongated hub is formed of a shape memory material which takes the deployed configuration when the elongated hub is exposed to body temperature.

15. The medical device of claim 12, wherein the elongated hub is formed of a shape memory material.

16. The medical device of claim 12, wherein the plurality of magnetic members are fixed to the elongated hub.

17. The medical device of claim 12, wherein the plurality of magnetic members and the elongated hub include corresponding tabs and detents to maintain the positions of the plurality of magnetic members along the elongated hub.

18. The medical device of claim 12, wherein each of the plurality of magnetic members includes a jacket attached to a side thereof, each jacket projecting beyond the side to define an edge.

19. The medical device of claim 18, wherein each edge contacts the edges of adjacent jackets to form a continuous annular edge in the deployed configuration.

* * * * *